United States Patent [19]

Ball et al.

[11] Patent Number: 4,492,772
[45] Date of Patent: Jan. 8, 1985

[54] PROCESS FOR THE PRODUCTION OF OXYGENATED HYDROCARBONS BY THE CATALYTIC CONVERSION OF SYNTHESIS GAS

[75] Inventors: William J. Ball, Capel; Leonard Cotton; David G. Stewart, both of Epsom, all of England

[73] Assignee: The British Petroleum Company, London, England

[21] Appl. No.: 434,055

[22] Filed: Oct. 13, 1982

[30] Foreign Application Priority Data

Oct. 17, 1981 [GB] United Kingdom ............... 8131380

[51] Int. Cl.³ .............................................. C07C 27/06
[52] U.S. Cl. .................................... 518/713; 518/714; 518/716
[58] Field of Search ..................... 518/713, 716, 714

[56] References Cited

FOREIGN PATENT DOCUMENTS 0030110  6/1981  European Pat. Off. ............ 518/713

OTHER PUBLICATIONS

Bhasin et al., J. of Catalysis, 54, 120–128, (1978).

Primary Examiner—Howard T. Mars
Attorney, Agent, or Firm—Brooks, Haidt, Haffner & Delahunty

[57] ABSTRACT

An oxygenated hydrocarbon product comprising methanol and ethanol is produced by hydrogenating carbon monoxide at a temperature in the range 150° to 450° C. and a pressure in the range 1 to 700 bars in the presence as catalyst of a supported mixture of the metals rhodium, silver, zirconium and molybdenum and optionally also one or more of the metals iron, manganese, rhenium, tungsten, ruthenium, chromium, thorium and potassium. The preferred support is silica.

10 Claims, 1 Drawing Figure

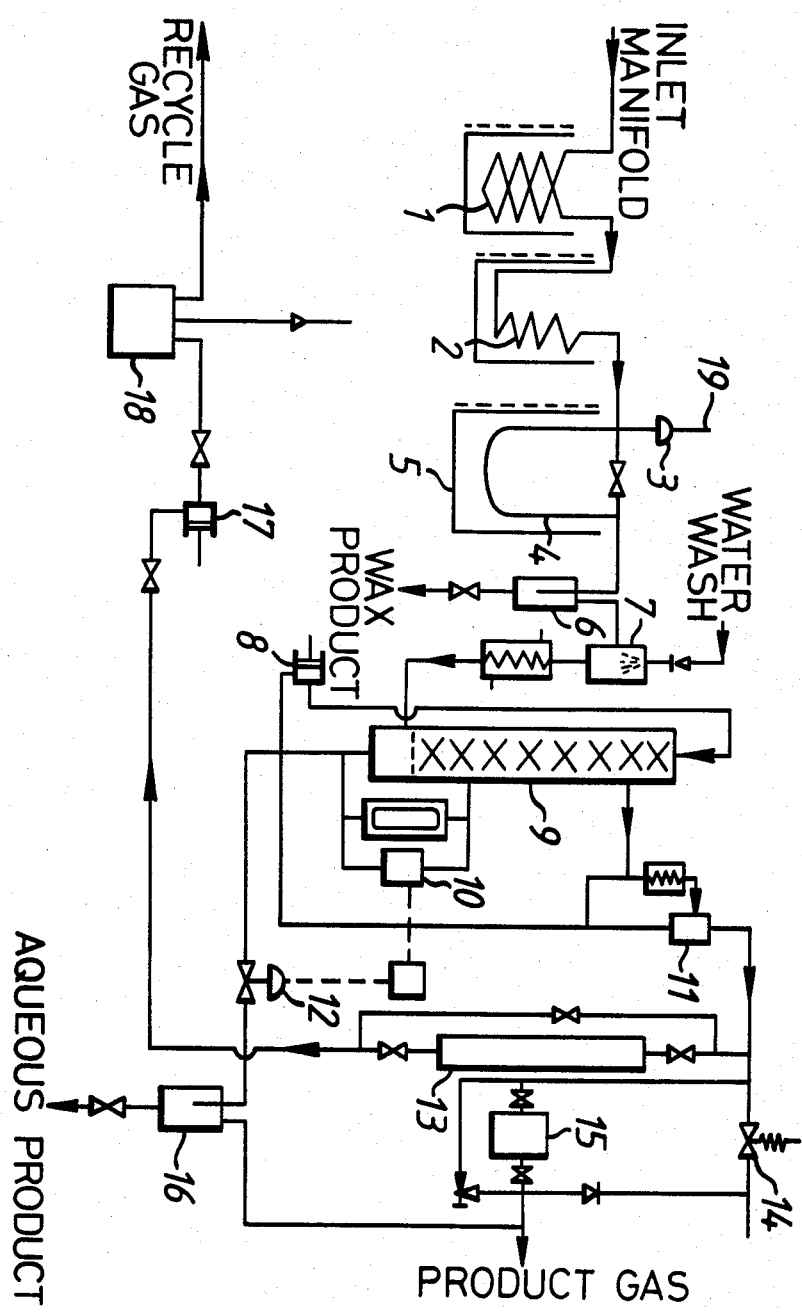

PROCESS FOR THE PRODUCTION OF OXYGENATED HYDROCARBONS BY THE CATALYTIC CONVERSION OF SYNTHESIS GAS

The present invention relates generally to the production of oxygenated hydrocarbons and in particular to a process for the production of an oxygenated hydrocarbon product comprising methanol and ethanol by the catalytic conversion of carbon monoxide and hydrogen mixtures, hereinafter to be referred to as synthesis gas.

Alcohols are gaining increasing importance as gasoline supplements and automotive fuels. In some countries there are plans for satisfying the increased demand by fermentation of natural products, e.g. molasses and beet, but worldwide there is a growing recognition of the need for an inexpensive mixed alcohols process. Potentially the catalytic conversion of synthesis gas offers just such a process. Synthesis gas can readily be obtained not only from crude oil but also from coal and methane gas which is potentially available in vast quantities.

Much of the early work on synthesis gas conversion involved the use as catalysts of the metals of Group VIII of the Periodic Table such as iron, cobalt, nickel and ruthenium and various other metal oxide systems. One general disadvantage of such systems is that catalysts which possess acceptable activity generally tend to be unselective i.e. they produce a wide spectrum of products including both hydrocarbons and oxygenated hydrocarbons having a very broad distribution of carbon numbers. This not only complicates the recovery of the desired products but also results in wastage of reactants to undesirable products. On the other hand those catalysts having acceptable selectivity generally have a low activity thereby necessitating recycle of large quantities of unchanged reactants.

In U.S. Pat. No. 4246186 (Union Carbide Corp.) there is disclosed a process which, it is claimed, overcomes the aforesaid disadvantages of the prior art processes. The process for selectively producing $C_2$ oxygenated hydrocarbons involves continuously contacting synthesis gas with a heterogeneous catalyst essentially comprising rhodium metal under reaction conditions correlated so as to favour the formation of a substantial proportion of acetic acid, ethanol and/or acetaldehyde. Subsequent patent applications describe the production of ethanol and/or acetic acid by contacting synthesis gas with a rhodium/iron catalyst (U.S. Pat. No. 4235801), a rhodium/manganese catalyst (U.S. Pat. No. 4014913), a rhodium/molybdenum or rhodium/tungsten catalyst (U.S. Pat. No. 4,096,164), a rhodium/ruthenium catalyst (U.S. Pat. No. 4,101,450), and a rhodium/uranium/thorium catalyst (U.S. Pat. No. 4162262).

We have described and claimed processes for the conversion of synthesis gas to oxygenated hydrocarbons in the presence of catalysts comprising rhodium/chromium (European application publication No. 18763), rhodium/zirconium (European application publication No. 30110), rhodium/rhenium (UK application publication No. 2078745) and rhodium/silver (European application publication No. 45620).

It has now been found that a supported mixture of the metals rhodium, silver, zirconium and molybdenum, optionally in combination with other metals, is a particularly effective catalyst for the conversion of synthesis gas to oxygenated hydrocarbons comprising methanol and ethanol.

Accordingly, the present invention provides a process for the production of an oxygenated hydrocarbon product comprising methanol and ethanol which process comprises contacting synthesis gas at a temperature in the range of 150° to 450° C. and a pressure in the range 1 to 700 bars with a catalyst comprising a supported mixture of the metals rhodium, silver, zirconium and molybdenum.

Mixtures of the gases hydrogen and carbon monoxide are abundantly available in the form of synthesis gas. Methods for preparing synthesis gas are well-known in the art and usually involve the partial oxidation of a carbonaceous substance, e.g. coal. Alternatively synthesis gas may be prepared, for example, by the catalytic steam reforming of methane. Although it is preferred to use substantially pure synthesis gas the presence of such impurities as carbon dioxide and nitrogen can be tolerated. On the other hand impurities which have a deleterious effect on the reaction should be avoided. The ratio of hydrogen to carbon monoxide in the synthesis gas may vary widely. Normally the molar ratio of hydrogen to carbon monoxide may be in the range of from 20:1 to 1:20, preferably from 5:1 to 1:5. Methods for adjusting the molar ratio of hydrogen to carbon monoxide by the so-called 'shift reaction' are well-known to those versed in the art.

The catalyst comprises a supported mixture of the metals rhodium, silver, zirconium and molybdenum. A wide variety of support materials may be employed. Suitable support materials include silica, alumina, silica/alumina, magnesia, thoria, titania, chromia, zirconia and active carbon, of which silica is preferred. Zeolite molecular sieves and in particular the crystalline zeolites may also be employed. Suitably the support has a relatively high surface area. The support may have a surface area up to 350 square meters per gram (BET low temperature nitrogen adsorption isotherm method), preferably in the range 1 to 300 square meters per gram. Whilst the actual form of the metal components under the reaction conditions is not known with any degree of certainty it is likely that they are in either the oxide form or in the metallic form under the reducing conditions prevailing. Thus the metals may be added in the form of the metals themselves or in the form of metal compounds and may be added concurrently or sequentially. The metals may be deposited on the support by any of the techniques commonly used for catalyst preparation. Although it is possible to add particles of the metals to the support it is preferred to use the techniques of impregnation from an organic or inorganic solution, precipitation, coprecipitation or cation exchange. Conveniently the catalyst may be prepared by impregnating the support with a solution of inorganic or organic metal compounds. Suitable compounds are the salts of the metals e.g. the halides, particularly the chlorides and nitrates. Following impregnation the catalyst is preferably dried and calcined. The amount of each of the metals on the support may suitably be in the range of from 0.01 to 25 weight percent, preferably from 0.1 to 10 weight percent, based on the combined weight of the metals and the support. The relative proportions of each of the metals may be varied over a wide range. The catalyst may be further improved by incorporating on the support a cocatalyst comprising one or more other metals selected from Groups I to VIII of the Periodic Table. Suitable metals include iron, manganese, rhenium, tungsten, ruthenium, chromium, thorium, and potassium. Each additional metal component may be present in an amount in the range of 0.1 to 10 weight percent based on the combined weight of the metals and the support.

In another embodiment of the present invention the support can be activated by the addition of one or more metal or non-metal activator components followed by calcination prior to incorporation of the metals rhodium, silver, zirconium and molybdenum and, optionally, other metals. Whilst a wide variety of such metals and non-metals may be added, the alkali metals, thorium, manganese, rhodium, iron, chromium, molybdenum, zirconium, rhenium, silver, boron and phosphorus are specific examples of such materials. Any of the known techniques for catalyst preparation hereinbefore referred to may be used for addition of the activating material. In the case of a metal activator the support is preferably impregnated with a solution of a compound of the metal, suitably the nitrate or chloride, and is thereafter dried, suitably by evaporation and calcined. The activated support is then in a suitable condition for the addition of the metals rhodium, silver, zirconium and molybdenum. The amount of activator compound added may suitably be in the range 0.01 to 50 weight percent, preferably from 1 to 25 weight percent based on the combined weight of the activator component and the support.

With regard to the reaction conditions the temperature is preferably in the range from 200° to 400° C. and even more preferably from 220° to 350° C.; the use of higher temperatures within the aforesaid ranges tends to increase the co-production of methane. Because of the highly exothermic nature of the reaction the temperature requires careful control in order to prevent a runaway methanation, in which methane formation increases with increasing temperature and the resulting exotherm increases the temperature still further. In fixed bed operations, temperature control may be achieved by mixing the catalyst with an inert diluent, thereby ensuring that the exothermic heat is more evenly distributed. In this way the useful life of the catalyst may be protected and prolonged. The reaction pressure is preferably in the range from 20 to 300 bars. The use of higher pressures within the aforesaid ranges increases the production rate and selectivity to oxygenated hydrocarbons.

An important reaction parameter is the conversion. A low conversion per pass, preferably less than 20% of the carbon monoxide, favours the formation of oxygenated hydrocarbons. A low conversion may suitably be achieved in a continuous process by employing a high space velocity. Suitably the gas hourly space velocity (volume of synthesis gas, at STP, per volume of catalyst per hour) is greater than $10^3$ per hour, preferably the gas hourly space velocity is in the range from $10^4$ to $10^6$ per hour. Excessively high space velocities result in an uneconomically low conversion while excessively low space velocities result in a loss of selectivity to desirable products.

Although the reaction may be carried out batchwise it is preferably carried out in a continuous manner.

The effluent from the reaction may be freed from the desired oxygenated products by various means, such as scrubbing and/or distillation. The residual gas which consists mainly of unreacted synthesis gas may be mixed with fresh carbon monoxide and hydrogen to give the required reactor feed and this composite gas then recycled to the reactor inlet.

The oxygenated hydrocarbon product produced in the presence of a catalyst consisting of rhodium, silver, zirconium and molybdenum supported on silica principally comprises a mixture of methanol and ethanol and possibly also propanol. the relative proportions of the $C_1$ to $C_3$ alcohols may be altered if desired by incorporating a fifth metallic component into the catalyst and/or by altering the relative proportions of the metals in the catalyst and/or by varying the nature of the support.

As hereinbefore mentioned oxygenated hydrocarbons such as mixtures of alcohols are useful both as automotive fuels and as automotive fuel supplements.

In another aspect therefore the present invention provides an internal combustion engine fuel composition comprising a major proportion of an automotive fuel and a minor proportion of the oxygenated hydrocarbon product as produced by the process hereinbefore described.

The process of the invention will now be illustrated by the following Examples and by reference to the accompanying FIGURE which is a simplified flow diagram of the apparatus employed.

With reference to the FIGURE, 1 is a preheated (150° C.), 2 is a preheater (200° C.), 3 is a bursting disc, 4 is a reactor, 5 is a salt pot, 6 is a knock-out pot, 7 is a water quench, 8 is a water recycle pump, 9 is a water wash tower, 10 is a DP level controller, 11 is a knockout pot, 12 is a Foxboro valve, 13 is a molecular sieve drier, 14 is a Gyp relief valve, 15 is a back pressure regulator, 16 is an aqueous product receiver, 17 is a gas recycle pump, 18 is a ballast vessel and 19 is a vent.

Also in the Examples the terms CO conversion and selectivity will be used. For the avoidance of doubt these are defined as follows:

$$\text{CO conversion} = \frac{\text{Moles of carbon monoxide consumed}}{\text{Moles of carbon monoxide fed}} \times 100$$

$$\text{Selectivity} = \frac{\text{Moles of carbon monoxide converted to particular product}}{\text{Moles of carbon monoxide consumed}} \times 100$$

Catalyst Preparation

Catalyst A - 1.95% Mo/4.88% Ag/4.35% Zr/3.34% Rh/SiO$_2$

Silver nitrate (0.9g) was dissolved in deionised water (20 ml) and the solution added to Davison silica, grade 59 (10 g, 8–16 mesh granules). The mixture was evaporated to dryness on a steam-bath and the dry product reduced in hydrogen at 450° C. for 6 hours.

Zirconium tetrachloride (1.3 g) and rhodium trichloride trihydrate (1.0 g) were dissolved in deionised water (50 ml) and the resulting solution added to the silver-silica support. The mixture was evaporated to dryness on a steam-bath and the dry product reduced in hydrogen at 450° C. for 6 hours.

Ammonium heptamolybdate tetrahydrate (0.48 g) was dissolved in deionised water (20 ml) and the resulting solution added to the above treated support. The mixture was evaporated to dryness on a steam bath and the dry product heated at 450° C. in hydrogen for 6 hours.

Catalyst B - 1.97% Mo/4.93% Ag/4.39% Zr/2.52% Rh/SiO$_2$

The catalyst was prepared as described for Catalyst A using silver nitrate (0.9 g), zirconium tetrachloride (1.3 g), rhodium trichloride trihydrate (0.75 g), ammonium heptamolybdate tetrahydrate (0.42 g) and Davison silica, grade 59 (10 g).

Catalyst C - 1.98% Mo/4.97% Ag/4.42% Zr/1.7% Rh/SiO$_2$

The catalyst was prepared as described for Catalyst A using silver nitrate (0.9 g), zirconium tetrachloride (1.3 g), rhodium trichloride trihydrate (0.5 g), ammonium heptamolybdate tetrahydrate (0.42 g) and Davison silica, grade 59 (10 g)

Catalyst D (rhodium/silver/zirconium/molybdenum)

Silver nitrate (2.7 g) was dissolved in deionised water (50 ml) and the solution added to Davison silica, grade 59 (30 g, 8-16 mesh granules). The mixture was evaporated to dryness on a steam bath and the dry product reduced in hydrogen at 450° C. for 6 hours.

Zirconium tetrachloride (3.9 g) and rhodium trichloride trihydrate (3.9 g) were dissolved in deionised water (50 ml) and the resulting solution added to the silver-silica support. The mixture was evaporated to dryness on a steam-bath and the dry product reduced in hydrogen at 450° C. for 6 hours.

Ammonium heptamolybdate tetrahydrate (1.26 g) was dissolved in deionised water (50 ml) and the resulting solution added to the above treated support. The mixture was evaporated to dryness on a steam bath and the dry product heated at 450° C. in hydrogen for 6 hours. Catalyst E - 5% Rh/SiO$_2$ Rhodium trichloride trihydrate (8.1 g) was dissolved in hot deionised water (200 ml) and the resulting solution was added to Davison silica, grade 57 (60 g, 8-16 mesh granules). The mixture was evaporated to dryness on a steam-bath and the solid dried at 120° C. for 16 hours. The catalyst was reduced in hydrogen at 450° C. for 16 hours.

Catalyst F - 4.8% Rh/4.6% Zr/SiO$_2$

Rhodium trichloride trihydrate (8.1 g) and zirconium tetrachloride (7.8 g) were dissolved in deionised water (200 ml) and the resulting solution was added to Davison silica, grade 57 (60 g, 8-16 mesh granules). The mixture was evaporated to dryness on a steam-bath with stirring and the solid dried at 120° C. for 16 hours. The catalyst was reduced in hydrogen at 450° C. for 16 hours.

Catalyst G - 4.75% Rh/5.15% Ag/SiO$_2$

Rhodium trichloride trihydrate (8.1 g) was dissolved in deionised water (150 ml).

Silver nitrate (5.4 g) was dissolved in deionsed water (150 ml).

The silver nitrate solution was added to Davison silica, grade 57 (60 g, 8-16 mesh granules) and the whole was evaporated to dryness on a steam-bath. The material was dried at 120° C. for 16 hours and reduced in hydrogen at 450° C. for 6 hours. The rhodium trichloride solution was then added to the silver-silica composite prepared as above and the whole was evaporated to dryness on a steam-bath. The solid was dried at 120° C. for 16 hours and reduced in hydrogen at 450° C. for 6 hours.

Catalyst H - 2.4% Rh/2.2% Mo/SiO$_2$

Ammonium heptamolybdate tetrahydrate (0.42 g) and rhodium trichloride trihydrate (0.65 g) were dissolved in deionised water (20 ml) and added to Davison silica, grade 59 (10 g, 8-16 mesh granules). The mixture was evaporated to dryness on a steam-bath and dried at 120° C. for 16 hours. The catalyst was reduced in hydrogen at 450° C. for 5 hours.

Catalyst Testing

Example 1

With reference to the accompanying FIGURE a mixture of carbon monoxide and hydrogen in a molar ratio of 1:2 was passed via the inlet manifold through the two preheater coils (1) and (2) maintained at 150° C. and 200° C. respectively in silicone oil baths. The heated gases were then fed via a heat-traced line to the copper lined reactor (4) which was maintained at 50 bars pressure and contained a fixed bed of Catalyst A in the form of 8-16 mesh (BSS) granules. The reactor was maintained at the desired reaction temperature by immersion in a molten salt bath (5). The product gases were passed via a heat-traced line through a knock-out pot for wax products (6) to a small quench vessel (7) into the top of which water was sprayed. The gases were then passed through a water cooler to the bottom of the water wash tower (9) which was packed with 3/8 inch Raschig rings. In the tower (9) the product gases were washed counter-current with water. The resulting liquid product was fed into the receiver (16) and any dissolved gases were recombined with the product gas stream from the back pressure regulator (15). The separated gas stream from the top of the water wash tower (9) was passed through a water cooler to the knock-out pot (11) and then to the inlet side of the dome-loaded back pressure regulator (15). Recycle gas was recovered from the inlet side of the back pressure regulator (15), passed through a molecular sieve drier (13) and compressed up to 67 bars in the gas ballast vessel (18) using the gas recycle pump (17). The recycle gas was fed back to the inlet manifold. Provision was made to feed spot samples of the inlet gases and the total gas stream to a gas chromatographic analytical unit.

The product gas stream leaving the back pressure regulator (15) was measured and samples were withdrawn and analysed by gas chromatography.

When the reactor had reached equilibrium a balanced run was carried out over a one hour period.

The reaction conditions and the results obtained are given in the accompanying Table 1.

Example 2

Example 1 was repeated except that Catalyst B was used in place of Catalyst A.

Example 3

Example 1 was repeated except that Catalyst C was used in place of Catalyst A.

The reaction conditions and the results of Examples 2 and 3 are given in Table 1.

Example 4

Example 1 was repeated except that Catalyst D was used in place of Catalyst A.

The reaction conditions and the results obtained are given in Table 2.

Comparison Test 1

Example 1 was repeated except that Catalyst E was used in place of Catalyst A.

Comparison Test 2

Example 1 was repeated except that Catalyst F was used in place of Catalyst A.

Comparison Test 3

Example 1 was repeated except that Catalyst G was used in place of Catalyst A.

Comparison Test 4

Example 1 was repeated except that Catalyst H was used in place of Catalyst A.

The reaction conditions and the results of Comparison Tests 1 to 4 are given in the accompanying Table 3.

Comparison Tests 1 to 4 are not examples according to the present invention because the catalyst was deficient in one or more of the metals molybdenum, silver and zirconium. They are included for the purpose of comparison.

We claim:

1. A process for the production of an oxygenated hydrocarbon product comprising methanol and ethanol which process comprises contacting synthesis gas at a temperature in the range 150° to 450° C. and a pressure in the range 1 to 700 bars with a catalyst comprising a mixture of the metals rhodium, silver, zirconium and molybdenum incorporated on the same support.

2. A process according to claim 1 wherein the support is either silica, alumina, silica-alumina, magnesia, thoria, titania, chromia, zirconia or active carbon.

3. A process according to claim 1 wherein the support is silica.

4. A process according to claim 1 wherein the support is a crystalline zeolite.

5. A process according to any one of the previous claims wherein the amount of each of the metals on the support is in the range from 0.1 to 10 weight percent.

6. a process according to claim 5 wherein there is incorporated on the support a cocatalyst comprising one or more of the metals iron, manganese, rhenium, tungsten, ruthenium, chromium, thorium and potassium in an amount in the range from 0.1 to 10 weight percent

TABLE 1

Reaction Parameters: Feed = CO:H$_2$:1:2 (molar)
Pressure: 50 bar
Recycle ratio: 10:1
GHSV: 24000

| Ex | Catalyst | Reaction Temperature °C. | CO Conversion % | Selectivity % | | | | | | | Productivity g mole/hr/liter of catalyst |
|---|---|---|---|---|---|---|---|---|---|---|---|
| | | | | CO$_2$ | Methane | Ethane | Propane | Methanol | Ethanol | nPropanol | |
| 1 | A | 275 | 52.5 | 4.4 | 24.2 | 3.5 | 1.6 | 52.1 | 14.0 | 0.2 | 10.3 |
| | | 285 | 54.5 | 4.0 | 31.2 | 4.3 | 2.0 | 44.8 | 12.5 | 1.3 | 9.3 |
| 2 | B | 275 | 46.9 | 3.7 | 20.5 | 3.1 | 1.4 | 55.2 | 14.4 | 1.8 | 9.5 |
| | | 285 | 46.6 | 4.2 | 29.2 | 4.3 | 2.0 | 47.7 | 11.5 | 1.2 | 9.3 |
| 3 | C | 275 | 29.9 | 2.8 | 15.5 | 2.6 | 1.9 | 65.8 | 10.8 | 0.5 | 5.8 |
| | | 285 | 22.0 | 4.2 | 30.2 | 4.8 | 2.3 | 49.0 | 9.4 | — | 4.2 |
| | | 310 | 29.2 | 4.6 | 34.7 | 5.6 | 2.6 | 43.9 | 8.7 | — | 4.8 |

TABLE 2

Catalyst: Catalyst D
Reaction Parameters: H$_2$:CO molar ratio = 2:1
pressure = 50 bars

| Reaction Temp °C. | Recycle Gas ratio | GHSV hr$^{-1}$ | CO con % | Selectivity % | | | | | | | | Productivity g mole/hr/liter of cat |
|---|---|---|---|---|---|---|---|---|---|---|---|---|
| | | | | Methane | Ethane | Propane | CO$_2$ | Methanol | Ethanol | n-Propanol | Methyl Acetate | |
| 250 | 19:1 | 22500 | 64 | 14 | 1 | 1 | 2 | 60 | 17 | 3 | 2 | 7.6 |
| 260 | 18:1 | 22500 | 70 | 17 | 2 | 2 | 3 | 55 | 17 | 3 | 1 | 8.1 |
| 270 | 20:1 | 48600 | 69 | 19 | 3 | 1 | 3 | 53 | 17 | 3 | 1 | 14.8 |
| 275 | 14:1 | 47000 | 65 | 26 | 3 | 2 | 2 | 48 | 16 | 2 | 1 | 17.2 |

TABLE 3

Reaction parameters: Feed:CO:H$_2$ = 1:2 (molar)
Pressure: 50 bar
Recycle ratio: 10:1
GHSV: 24000

| Comp Test | Catalyst | Reaction Temperature °C. | CO Conversion % | Selectivity % | | | | | | | | | | | Productivity g mole/hr/l of catalyst |
|---|---|---|---|---|---|---|---|---|---|---|---|---|---|---|---|
| | | | | CO$_2$ | CH$_4$ | C$_2$ | C$_3$ | MeOH | EtOH | PrOH | BuOH | Acet | Acetic acid | Esters | |
| 1 | E | 275 | 12.5 | 4.2 | 29.2 | 5.1 | 6.1 | 18.6 | 20.8 | 4.0 | 2.2 | 5.4 | 3.2 | — | 1.16 |
| | | 290 | 16.8 | 6.6 | 31.7 | 5.4 | 5.5 | 15.8 | 18.3 | 4.4 | 2.3 | 7.8 | 1.9 | — | 1.40 |
| | | 310 | 24.5 | 6.1 | 42.4 | 6.5 | 6.2 | 12.8 | 15.2 | 2.5 | 1.7 | 5.4 | 1.2 | — | 1.81 |
| 2 | F | 260 | 23.4 | 6.9 | 46.8 | 1.0 | 1.2 | 11.9 | 25.9 | — | — | — | — | 6.5 | 2.12 |
| | | 270 | 21.7 | 3.2 | 40.6 | 1.7 | 1.7 | 7.6 | 26.5 | 0.8 | — | 8.3 | 1.4 | 7.8 | 2.03 |
| | | 280 | 26.3 | 3.8 | 46.0 | 1.6 | 1.7 | 6.7 | 24.3 | 0.9 | — | 5.8 | 1.4 | 7.4 | 2.38 |
| 3 | G | 310 | 11.0 | 2 | 33.0 | 3 | — | 11.0 | 30.0 | 3.0 | — | 14.0 | 4.0 | — | 1.09 |
| 4 | H | 280 | 7.9 | 13.4 | 26.5 | 8.6 | — | 33.5 | 12.2 | 2.9 | 1.0 | 0.8 | 0.5 | 0.5 | 1.68 |
| | | 290 | 9.7 | 15.3 | 29.6 | 9.4 | — | 27.4 | 9.6 | 4.7 | 0.4 | 0.4 | 1.8 | 1.5 | 1.84 |
| | | 300 | 12.0 | 18.0 | 32.8 | 10.5 | — | 25.7 | 7.9 | 2.2 | 0.3 | 0.3 | 1.4 | 0.8 | 1.99 | based on the combined weight of the metals and the support.

7. A process according to claim 5 wherein the temperature is in the range from 200° to 400° C.

8. A process according to claim 5 wherein the pressure is in the range from 20 to 300 bars.

9. A process according to claim 5 when operated in continuous manner at a gas hourly space velocity greater than $10^3$ per hour.

10. A process according to claim 9 wherein the gas hourly space velocity is in the range from $10^4$ to $10^6$ per hour.

* * * * *